United States Patent [19]
Childress

[11] Patent Number: 5,466,848
[45] Date of Patent: Nov. 14, 1995

[54] PROCESS FOR THE PREPARATION OF SILANE POLYSULFIDES

[75] Inventor: Thomas E. Childress, Newport, Ohio

[73] Assignee: OSi Specialties, Inc., Danbury, Conn.

[21] Appl. No.: 314,204

[22] Filed: Sep. 28, 1994

[51] Int. Cl.$^6$ .................................................. C07F 7/04
[52] U.S. Cl. ........................... 556/427; 556/428; 525/102
[58] Field of Search ..................................... 556/427, 428

[56] References Cited

U.S. PATENT DOCUMENTS

| | | | |
|---|---|---|---|
| 3,842,111 | 10/1974 | Meyer-Simon et al. | 260/448.2 R |
| 3,946,059 | 3/1976 | Janssen et al. | 260/448.2 R |
| 4,072,701 | 2/1978 | Pletka et al. | 260/448.8 R |
| 4,129,585 | 12/1978 | Buder et al. | 260/448.8 R |
| 4,292,234 | 9/1981 | Borel | 556/427 |
| 4,507,490 | 3/1985 | Panster et al. | 556/427 |
| 4,640,832 | 2/1987 | Bittner et al. | 423/562 |

OTHER PUBLICATIONS

Thomas, J. S. and Rule, A. J. Chem. Soc. 103, 871–6: Proc. Chem. Soc. 29, 154–5.

*Primary Examiner*—Mark Sweet
*Attorney, Agent, or Firm*—Andrew S. Reiskind

[57] ABSTRACT

Sulfur-containing organosilicon compounds useful as coupling agents in vulcanizable rubbers to enhance various properties, including low rolling resistance for automobile tires, are prepared. Preferred compounds include Ω, 106′-bis (trialkoxysilylalkyl) polysulfides. In the preferred process scheme, sodium ethoxylate is reacted with hydrogen sulfide gas to yield sodium sulfide. The sodium sulfide is then reacted with sulfur to form the tetrasulfide. The product of that reaction is then reacted with chloropropyltriethoxysilane to form the compound 3,3′- bis (triethoxysilylpropyl) tetrasulfide. The use of hydrogen sulfide gas and sodium metal alcoholates provides an efficient and economical process.

10 Claims, 1 Drawing Sheet

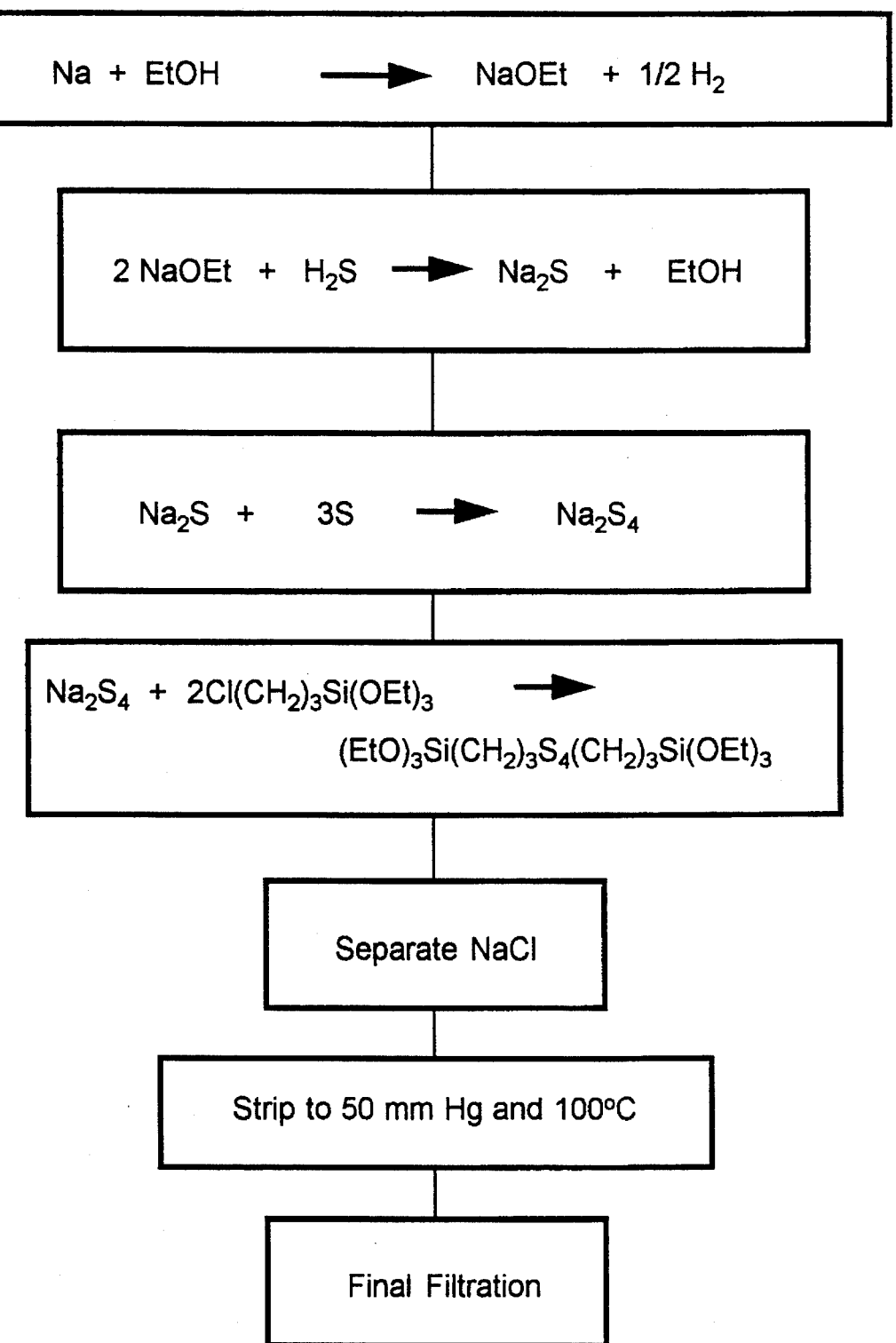
FIG.

PROCESS FOR THE PREPARATION OF SILANE POLYSULFIDES

TECHNICAL FIELD

The invention is directed to the preparation of sulfur-containing organosilicon compounds useful as coupling agents in vulcanizable rubbers to enhance products made from them. In its preferred form, the invention improves the preparation of $\Omega$, $\Omega'$-bis (trialkoxysilylalkyl) polysulfides.

Sulfur-containing organosilicon compounds have found widespread use in a variety of rubber products in the last two decades. Uses include tire walls and bodies, rubber hoses, rubber belts, and numerous other rubber products. Depending on the formulation, selected properties of the rubber can be modified.

Since the early 1980's, automobile manufacturers have been encouraging the production of low-rolling-resistance tires. A number of sulfur-containing organosilicon compounds have been identified as useful in this regard. The improvements obtainable could be helpful in meeting federal fuel economy standards without sacrificing wet traction and wear. Silane polysulfide coupling agents, such as 3,3'-bis (triethoxysilylpropyl) tetrasulfide, have been proposed for use in low-rolling-resistance tires.

To achieve optimum effect, it has been found that each low-rolling-resistance tire should contain several ounces of this or another suitable silane.

There is a need for a new process to produce organosilane polysulfides effective for use in low-rolling-resistance tires, and other uses, in good yield to permit economical production of large quantities with controllable safety and environmental impact.

BACKGROUND ART

The art of manufacturing organosilane polysulfides is well established, with the art offering a variety of processing strategies.

Meyer-Simon, Schwarze, Thurn, and Michel disclose the reaction of a metal polysulfide with an $\Omega$-chloroalkyltrialkoxysilane in U.S. Pat. No. 3,842, 111. Example 2 shows the preparation of 3,3'-bis (triethoxysilylpropyl) tetrasulfide by reacting $Na_2S_4$ with 3-chloropropyltriethoxysilane in absolute ethanol. The procedure for preparing the metal polysulfide is not exemplified.

In U.S. Pat. No. 4,072,701, Pletka describes the preparation of these compounds by first heating 3-chloropropyltrichlorosilane (Example 1) with ethanol, and then adding both sulfur and NaSH. The reaction developed gaseous hydrogen sulfide in situ, but some of the sulfur therein was not recoverable (see, U.S. Pat. No. 4, 129,585, col. 1, lines 32–34, in this regard). Therefore, the yields based on added sulfur tended to be low. Also, the use of NaHg is problematic due to its deliquescent nature and its tendency to oxidize to sulfate. The deliquescence is troublesome from the standpoint that it increases the risk that water will enter the reaction and cause hydrolysis of the alkoxide reactants.

After describing the above two patents in U.S. Pat. No. 4,129,585, Buder, Pletka, Michel, Schwarz and Düsing, describe a procedure for making the noted compounds without the production of gaseous hydrogen sulfide. The process entails reacting a suitable alkali metal alcoholate, e.g., sodium ethoxide, in preferably alcoholic solution with a desired $\Omega$-chloroalkyltrialkoxysilane, a suitable metal hydrogen sulfide, and sulfur. The resulting product was purified by separating the salt formed and distilling off the alcohol. Again, the use of the metal hydrogen sulfide can be a source of water entering the system unless precautions are taken.

In U.S. Pat. No. 4,507,490, Panster, Michel, Kleinschmidt and Deschler, first prepare $Na_2S$. Again, they employ a metal hydrogen sulfide but react it with an alkali metal, such as sodium, in a polar solvent, such as ethanol. This reaction is highly exothermic and evolves hydrogen gas. The process is said to eliminate the use of an alkali metal alcoholate solution, noting that its production requires such a great deal of time as to be industrially improbable. The $Na_2S$ is reacted with additional sulfur to form a desired polysulfide, preferably $Na_2S_4$. The polysulfide is then reacted with a desired $\Omega$-chloroalkyl trialkoxysilane, e.g., $Cl(CH_2)_3Si(OC_2H_5)_3$, to form the desired $\Omega$, $\Omega'$-bis (trialkoxysilylalkyl) polysulfide.

Janssen and Steffen, in U.S. Pat. No. 3,946,059, offer a distinct approach and criticize procedures of the type described above. They eliminate the production, and therefore separation, of salts formed in the above reactions by contacting a bis (alkylalkoxysilyl) disulfide with sulfur at a temperature between 100° and 200° C. This procedure, however, adds the difficulty of the high temperature processing and requires the initial preparation of bis-silyl disulfides by the reaction of sulfuryl chloride with silyl mercaptans.

While the possibility might appear to exist that commercial forms of alkali metal sulfides, e.g., sodium tetrasulfide, could be employed, this would not be practical. The commercial forms of sodium tetrasulfide include water which must be completely removed prior to contact with the alkoxylates. If water is present, the alkoxide is hydrolyzed and a polysiloxane polymer is formed. And, while Bittner, et al. teach in U.S. Pat. No. 4,640,832, the reaction of sodium salts with hydrogen sulfide in alcoholic solution, this route has been criticized as "quite inconvenient" (see Thomas, et al, at CA, 7, 2910 (1913)).

Thus, the prior art has found the use of hydrogen sulfide gas, the separation of sodium chloride and the preparation of metal alkoxylates to be problematic in the preparation of sulfur-containing organosilicon compounds, and did not recognize that there was possible a reaction scheme which efficiently and effectively combines all of them. The invention provides a process which combines these and still obtains high yields based on sulfur.

SUMMARY OF THE INVENTION

It is an object of the invention to provide an improved process for preparing sulfur-containing organosilicon compounds useful as coupling agents in vulcanizable rubbers.

It is a further object of a preferred aspect of the invention to provide an improved process for preparing $\Omega$, 106'-bis (trialkoxysilylalkyl) polysulfides useful in the preparation of a variety of rubber products, specifically including low-rolling-resistance tires.

These and other objects are achieved by the invention which provides a process for preparing silane polysulfides, the process comprising:

(a) contacting hydrogen sulfide gas with an active metal alkoxide solution, (b) reacting elemental sulfur with the product of step (a), and (c) reacting the product of step (b) with a halohydrocarbylalkoxysilane of the formula Q—R—X in which Q is

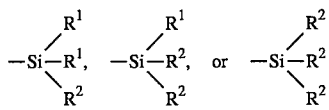

and in which

R¹ is an alkyl group of 1 to 4 carbon atoms or phenyl, and

R² is an alkoxy group with 1 to 8, preferably 1 to 4, carbon atoms, a cycloalkoxy group including 5 to 8 carbon atoms, or a straight or branched chain alkylmercapto group with 1 to 8 carbon atoms, wherein the various R¹ and R² groups can be the same or different, R is a divalent hydrocarbyl group including 1 to 18 carbon atoms, and X is a halogen, to produce a compound of the formula Q—R—S$_n$—R—Q in which Q and R are as defined above, and n is an integer of from 2 to 9, preferably from 3 to 5.

In the preferred embodiment, the product is 3,3'-bis (triethoxysilylpropyl) tetrasulfide, represented by the formula $(C_2H_5O)_3Si(CH_2)_3-S_4-(CH_2)_3Si(OC_2H_5)_3$, and is prepared by: (a) contacting an ethanol solution of sodium ethoxylate with hydrogen sulfide gas to produce a solution of Na$_2$S, (b) adding elemental sulfur to the solution of Na$_2$S in an amount sufficient to form Na$_2$S$_4$, and (c) adding Cl(CH$_2$)$_3$Si(OC$_2$H$_5$)$_3$ to the resulting reaction mixture and reacting to completion.

All parts and percentages in this description are on a weight basis and are based on the weight of the composition at the referenced stage of processing.

By the use of the process of the invention, silane polysulfides of high quality are prepared efficiently and in good yield.

BRIEF DESCRIPTION OF THE DRAWING

The invention will be better understood and its advantages will be more apparent when the following detailed description is read in light of the accompanying drawing, wherein:

The Figure is a flow chart illustrating a preferred process according to the invention.

DETAILED DESCRIPTION

The invention, which relates to the preparation of sulfur-containing organosilicon compounds useful for a variety of purposes, especially as coupling agents in vulcanizable rubbers, will be described with special reference to the preparation of a preferred class of compounds, the Ω, Ω'-bis (trialkoxysilylalkyl) polysulfides.

Among this class of compounds are a wide number of materials, including the various polysulfides listed below wherein the term polysulfide includes all of the di, tri, tetra, penta, hexa, hepta, octa, and nona-sulfides according to the following formulae:

bis (trimethoxysilylmethyl) polysulfides, bis (triethoxysilylmethyl) polysulfides, bis (dimethylethoxysilylmethyl) polysulfides, bis(tripropoxysilylmethyl) polysulfides, bis (tributoxysilylmethyl) polysulfides, bis (tripentoxysilylmethyl) polysulfides, bis (trihexoxysilylmethyl) polysulfides, bis (triheptoxysilylmethyl) polysulfides, and bis (trioctyloxysilylmethyl) polysulfides;

3,3'-bis (trimethoxysilylpropyl) polysulfides, 3,3'-bis (triethoxysilylpropyl) polysulfides, 3,3'-bis (dimethylethoxysilylpropyl)polysulfides, 3,3'-bis (tripropoxysilylpropyl) polysulfides, 3,3'-bis (tributoxysilylpropyl) polysulfides, 3,3'-bis (tripentoxysilylpropyl) polysulfides, 3,3'-bis (trihexoxysilylpropyl) polysulfides, 3,3'-bis (triheptoxysilylpropyl) polysulfides, and 3,3'-bis (trioctyloxysilylpropyl) polysulfides;

4,4'-bis (trimethoxysilylbutyl) polysulfides, 4,4'-bis (triethoxysilylbutyl) polysulfides, 4,4'-bis (dimethylethoxysilylbutyl) polysulfides, 4,4'-bis (tripropoxysilylbutyl) polysulfides, 4,4'-bis (tributoxysilylbutyl) polysulfides, 4,4'-bis (tripentoxysilylbutyl) polysulfides, 4,4'-bis (trihexoxysilylbutyl) polysulfides, 4,4'-bis (triheptoxysilylbutyl) polysulfides, and 4,4'-bis (trioctyloxysilylbutyl) polysulfides;

5,5'-bis (trimethoxysilylpentyl) polysulfides, 5,5'-bis (triethoxysilylpentyl) polysulfides, 5,5'-bis (dimethylethoxysilylpentyl) polysulfides, 5,5'-bis (tripropoxysilylpentyl) polysulfides, 5,5'-bis (tripentoxysilylpentyl) polysulfides, 5,5'-bis (tripentoxysilylpentyl) polysulfides, 5,5'-bis (trihexoxysilylpentyl) polysulfides, 5,5'-bis (triheptoxysilylpentyl) polysulfides, and 5,5'-bis (trioctyloxysilylpentyl) polysulfides;

Similarly, the 6,6'-bis (trialkoxysilylhexyl)polysulfides; the 7,7'-bis (trialkoxysilylheptyl) polysulfides; the 8,8'-bis (trialkoxysilyloctyl) polysulfides; the 9,9'-bis (trialkoxysilylnonyl) polysulfides; the 10, 10'-bis (trialkoxysilyldecyl) polysulfides; and the isomers of these are included. Indeed, this disclosure is meant to include, each of the individual compounds comprised of combinations of the various groups encompassed by the generic formula Q—R—S$_n$—R—Q wherein, Q, R and n are as defined above.

This description illustrates the production of the preferred compound, 3,3'-bis (triethoxysilylpropyl) tetrasulfide:

$(C_2H_5O)_3Si(CH_2)_3-S_4-(CH_2)_3Si(OC_2H_5)_3$ employing the reaction of sodium ethoxide (NaOC$_2$H$_5$) with hydrogen sulfide gas to obtain sodium sulfide (Na$_2$S). The sodium sulfide can then be reacted with additional sulfur to form the desired polysulfide. The overall procedure for preparing this compound is illustrated in the process flow diagram of the Figure and is described in the Example. In the drawing and at times in the following description, Et is used to designate an ethyl group and Me is used to designate a methyl group.

Preparation of the Active Metal Alkoxide

As noted above, the process can be used to prepare a large number of end products. For each of these it is necessary to start with an active metal alkoxide solution. The active metal alkoxide will have the formula M—R², wherein M represents an active metal and R² is as defined above. Among the preferred active metals are those of the alkali metal group, especially sodium and potassium. The most preferred is sodium. However, among the other metals useful are lithium, rubidium and cesium. Among the preferred alkoxides are those containing methoxy, ethoxy, n-propoxy, i-propoxy, n-butoxy, i-butoxy, 2-methoxyethoxy or 2-ethoxyethoxy groups.

The reaction is carried out in a suitable organic solvent compatible with the alkoxide. In principle, any polar organic solvent can be employed that reacts with neither the alkali or other metal nor with the organic silicon compounds to form an undesired byproduct.

Preferably, the organic solvent is a linear or branched alcohol having 1 to 5 carbon atoms, e.g., methyl, ethyl, propyl, butyl or pentyl alcohol, as well as iso-propyl alcohol, iso-butyl alcohol and 2-methoxyethanol. Also suitable are cycloalkyl alcohols having 5 to 8 carbon atoms, e.g., cyclopentyl alcohol, cyclohexyl alcohol, cyclooctyl alcohol, phenyl or benzyl alcohol. It is useful to employ the alcohol which in each case corresponds to the $R^2$ group. In a given case, advantageously there can also be used a mixture of these alcohols, e.g., when different $R^2$ groups are used in a compound. Particularly preferred are methanol and ethanol, preferably in absolute form. In the preferred process, sodium metal is reacted with ethanol to form an ethanolic solution of sodium ethoxylate.

The reaction of active metal, e.g., sodium metal, and a suitable alcohol, e.g., ethanol, is preferably conducted with an excess of alcohol to produce a metal alkoxide, e.g., sodium ethoxide, solution. The following equation summarizes the reaction:

$$M + R^2H \rightarrow MR^2 + \tfrac{1}{2}H_2$$

The sodium or other metal should be maintained free of contact with moisture. The manufacture of sodium methoxide has been described by Arend. (Arend, A. G., Perfumery Essent. Oil Record, 28, 372–75, 1947) The preferred sodium ethoxide reaction is similar, but slower than the sodium methoxide reaction.

The concentration of the sodium ethoxide solution may be as low as about 10 wt % and as high as its solubility limit, which is about 25 wt % at 25° C. A high concentration of sodium ethoxide is desirable, since better product yields for given reactor size are obtained. The typical concentration for commercially-available sodium ethoxide is about 21 wt %.

The H₂S-Active Metal Alkoxide Reaction

In this step, $H_2S$ (hydrogen sulfide) gas is reacted with the active metal alkoxide (e.g., sodium ethoxide) in a suitable solvent (e.g., ethanol) to produce a suitable active metal sulfide, e.g., $Na_2S$:

$$2MR^2 + H_2S \rightarrow M_2S + 2R^2H$$

This reaction can be performed in production quantities of from about 50 to about 5,000 pound batches. Continuous and semi-continuous processes can also be employed. Preferably, the reaction is carried out with an excess of ethanol, typically charging the preferred sodium ethoxide raw material as a 21 wt % solution in ethanol. The preferred reaction between hydrogen sulfide gas and sodium ethoxide employs a molar feed ratio of the hydrogen sulfide to the sodium ethoxide of 1:2.

The reaction is conveniently conducted in a semi-batch mode. First, all of the metal alkoxide is added to the reactor. Then, the reactor contents are heated to a temperature effective for reaction, in the preferred case discussed, within the range of from about 40° to about 60° C., e.g., about 50° C. The hydrogen sulfide gas is then fed to the reactor. The hydrogen sulfide feed rate is not critical, typically it will be of the order of one hour, but will vary with equipment and batch size. At the end of the reaction, most of the active metal sulfide is in solution. However, some solid active metal sulfide particles may be present. In general, it is desirable to keep the system agitated until the next step.

Preferably, the reactor is maintained at a temperature between about 40° and about 60° C. during the hydrogen sulfide addition to avoid discoloration. The reaction necessitates some degree of cooling. After the hydrogen sulfide addition is completed, it is desirable to purge out the feed conduit with nitrogen to prevent draw back of liquid. After the purge, the kettle is preferably cooled, e.g., to about −25° C., and then vented to atmospheric pressure through a reflux condenser to trap out any ethanol vapors while maintaining the kettle blanketed with nitrogen gas.

The system is preferably equipped with a scrubber or absorber for capturing hydrogen sulfide emissions. Strong sodium hydroxide is a good scrubbing medium. The reaction is preferably conducted in a mechanically agitated kettle to assure good gas-liquid mixing to facilitate the reaction of the hydrogen sulfide with the active metal alkoxide. The hydrogen sulfide gas is desirably fed substantially via a diptube or gas sparger located near or preferably below the agitator.

Stoichiometry is important. The desired ratio is one mole of hydrogen sulfide per two moles of active metal alkoxide, with a preferred accuracy of hydrogen sulfide addition being about ±3%.

Sulfur Addition and Reaction

After the hydrogen sulfide reaction is completed, the reaction mixture is cooled, e.g., to about 25° C., then sulfur, preferably in powdered form, is added to the reactor in an amount sufficient to form the desired active metal polysulfide. When the sulfur addition is complete, the reactor is reheated, e.g., to about 45° C. During this period, the system is preferably maintained at atmospheric pressure under a nitrogen blanket. For the preparation of sodium tetrasulfide from sodium sulfide, the molar feed ratio of sulfur to sodium sulfide is 3:1, but can be varied as needed to obtain polysulfides having from 2 to 9 sulfur atoms. During the heating, the following reaction occurs in the preferred embodiment:

$$Na_2S + 3S \rightarrow Na_2S_4$$

It is preferred to maintain agitation in the reactor after the sulfur addition, sufficient to insure solubilization and reaction. It is also preferred, during and after the sulfur addition, to keep air out of the kettle to avoid oxidation which may contribute to a darkening of product color.

Halohydrocarbyltrialkoxysilane

The process of the invention employs a halohydrocarbyltrialkoxysilane for reaction with the polysulfide as prepared above. These compounds meet the general formula Q—R—X in which Q and R are as defined above and X is a halogen, typically chlorine, but bromine, iodine and fluorine compounds can be effective. In this formula, and therefore also in the final product, the hydrocarbyl group R signifies methylene as well as preferably n-propylene, i-butylene, or n-butylene, but can also be n-pentylene, 2-methylbutylene, 3-methylbutylene, 1,3-dimethylpropylene, n-hexylene, or n-decylene.

Illustrative compounds within formula Q—R—X are 3-chloropropyltriethoxysilane, 3-bromopropyltriethoxysilane, chloromethyltrimethoxysilane, 3-chloropropyltrimethoxysilane, 3-chloropropyldiethoxymethylsilane, 3-chloropropylcyclohexoxydimethylsilane, 4-bromobutyldiethoxybenzylsilane, 4-chlorobutyltrimethoxysilane, 5-chloropentyldimethoxyphenylsilane, 3-bromo-i-butyltriethyoxysilane, 3-chloropropyldimethoxy-p-ethylphenylsilane, 3-chloropropylethoxymethylethylsilane, 5-chloro-n-pentyldiethoxycyclopentylsilane, 3-bromopropyldimethoxycyclopentoxysilane, 3-bromo-2-methylpropyldimethoxycycloocytylsilane, 3-chloropropyldiethoxy-2-methoxyethoxy-silane, 3-chloropropyldibutoxymethylsilane, 3-bromopropylphenyloxydimethoxysilane, 3-chloropropyl-di-i-butoxy-2-methylphenysilane, 4-chlorobutyldimethoxybenzyloxysilane, 3-chloropropyltributoxysilane, 3-chloropropyldiethoxyamylsilane, and 3-chloropropyldiethoxy-p-methylphenylsilane.

Again here, as in the case of the inclusion of compounds meeting the definition of the formula for the end products, this disclosure is meant to include each of the individual compounds comprised of combinations of the various groups encompassed by the generic formula Q—R—X in which Q, R and X are as defined above.

In the preferred form of the reaction, a chloroalkylalkoxysilane is reacted with the sodium polysulfide. The chloroalkylalkoxysilane can be purchased or prepared according to any of the techniques available to those of ordinary skill in the art. One preferred practice is to prepare it by transesterification of $Cl(CH_2)_3Si(OMe)_3$.

In an alternative embodiment of the invention, the methoxy ester can be employed to form 3,3'- bis (trimethoxyalkoxysilane) polysulfide, and this product can then be converted to the ethyl or higher ester by transesterification in situ.

According to the preferred procedure, $Cl(CH_2)_3Si(OEt)_3$ can be prepared by the following transesterification reaction, typically at a temperature of from about 70° to about 100° C. and atmospheric pressure using about 1000 to 2000 ppm para-toluenesulfonic acid:

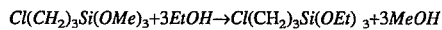

$Cl(CH_2)_3Si(OMe)_3 + 3EtOH \rightarrow Cl(CH_2)_3Si(OEt)_3 + 3MeOH$

This reaction is preferably run by continuously feeding ethanol while removing by-product methanol from the system to drive the equilibrium toward chloropropyltriethoxysilane. The reaction can conveniently begin at atmospheric pressure and reflux temperatures, i.e., a pot temperature of from about 80° to about 100° C. At the end of the reaction, the excess ethanol can be stripped off using vacuum and a somewhat higher temperature. A typical final condition for the ethanol strip would be a temperature of about 120° C. and a pressure of about 100 mm Hg.

Reaction of Active Metal Polysulfide with Halohydrocarbyltrialkoxysilane

The feed of halohydrocarbyltrialkoxysilane (preferably, chloroalkyltrialkoxysilane) to the reactor is preferably started as soon as a temperature of about 45° C. is reached after the sulfur addition as described above. The preferred reaction is:

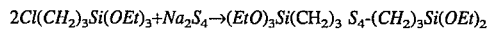

$2Cl(CH_2)_3Si(OEt)_3 + Na_2S_4 \rightarrow (EtO)_3Si(CH_2)_3S_4\text{-}(CH_2)_3Si(OEt)_3$ The molar feed ratio of chloropropyltriethoxysilane to $Na_2S_4$ is preferably 2:1. The reactor is preferably maintained at a temperature of about 45° C. while the chloropropyltriethoxysilane is being added to prevent accumulation of chloropropyltriethoxysilane. The chloropropyltriethoxysilane is preferably added at a rate such that the entire quantity is charged in a time period of from about 1 to about 3 hours, typically at least about 1 hour. If the duration is less than one hour, excessive chloropropyltriethoxysilane can accumulate in the reactor. Salt particles are formed during the reaction, and it is preferred to employ sufficient reactor agitation to maintain these in suspension. When the addition of the chloropropyltriethoxysilane is complete, the reactor is preferably heated to about 80° C. and held under reflux for a suitable time, e.g., from about 1 to about 3 hours, typically about 1.5 hours. After this period of reflux, the reactor is immediately cooled, e.g., to about 25° C.

Salt Removal

The reaction produces the desired product and also produces salt. In the preferred reaction, sodium chloride salt produced in the chloropropyltriethoxysilane addition step can be removed by filtering or centrifuging. If filtration is used, the media pore size should be about 5μ. Typically, no filter aid is necessary since the average particle size is fairly large, but one can be employed if needed. If centrifuging is employed, a basket or continuous scroll-type device can be employed.

The resulting filtercake will contain residual liquid product and can be washed, e.g., with ethanol to improve overall product yield.

Solvent Strip

The process preferably includes a step of stripping off detrimental levels of solvent, preferably reducing the solvent concentration to less than about 5% by weight. In the preferred process as described above, assuming an ethanol wash has not been used, the crude product contains about 60 wt % ethanol. Stripping, preferably in a single stage, can be employed to yield a product containing less than about 2 wt % ethanol. One suitable stripping technique is batch stripping of the crude material in a reactor, e.g., to a final condition of 100° C. and 50 mm Hg absolute pressure. A small quantity of salt may precipitate out during the ethanol strip, and it is preferred to subject the product to a final filtration as necessary to remove this.

EXAMPLE

The following example is presented for the purpose of further illustrating and explaining the invention, and is not to be taken as limiting in any regard. Unless otherwise indicated, all parts and percentages are based on the weight of the components at the indicated stage of processing.

This example describes the preparation of the preferred end product, 3,3'- bis (triethoxysilylpropyl) tetrasulfide. To accomplish this result, sodium ethoxide was prepared fresh, as was sodium tetrasulfide. The overall reaction is as illustrated in the Figure.

Preparation of sodium ethoxide

To a 500 ml glass reactor equipped with a feed funnel, a reflux column, a fritted glass sparge tube and thermometer, 13.97 grams of dry sodium chunks were added. Then, the reactor and the column were purged with $N_2$ for >5 minutes. Then, 188.33 grams of ethanol was charged into the feed funnel. During this step, the ethanol was added slowly enough to prevent the sodium from melting. After 85 minutes, all of the sodium was dissolved and the reactor was cooled from about 90° C. to about 40° C. for the next step.

H₂S Reaction with Sodium Ethoxide

Addition of hydrogen sulfide gas was started through a fritted glass sparge tube. The reaction was run with vigorous agitation during sparge. During a feed time of about 54 minutes, 10.31 grams of hydrogen sulfide gas was fed to the reactor.

Preparation of Na₂S₄

Following the above reaction, the reactor was cooled to 25° C. The reactor contents were water white. Some undissolved Na₂S particles were present.

To this reaction mixture was added 29.12 grams of sublimed sulfur. The reactor temperature was 25° C. After sulfur addition, the reactor contents turned dark in color. The reactor was sparged with N₂ for 6 minutes to remove any entrained air. The reactor was then heated to reflux, i.e., 78°–82° C. Heat up time from 25° to 82° C. was 13 minutes.

Preparation of Chloropropyltriethoxysilane

Chloropropyltrimethoxysilane was separately transesterified to the ethyl ester, chloropropyltriethoxysilane, in a 1 liter glass reactor equipped with a heating mantle, thermometer, ethanol addition funnel and a 5 tray, 1 inch diameter glass Oldershaw column. This column should have at least about 3 theoretical trays.

The reactor was initially charged with 527.15 grams of chloropropyltrimethoxysilane, 1.05 grams of p-toluenesulfonic acid (2000ppm), and 130 grams of ethanol. During the first part of the reaction the reactor temperature was run in the range 80°–90° C. Then the ethanol feedrate was cut back and the reactor was run at 98°–115° C., to help drive MeOH out of the reactor. A reflux ratio of about 8:1 was used for the entire run. The ethanol usage was 2.3 times the theoretical amount. The reaction was run for about 8.9 hours, over a two day period. High temperature (111 ° C.) at the end of the run helped assure a relatively low residual ethanol concentration, i.e., 6.7%. This material could be vacuum stripped to reduce the ethanol further.

| PRODUCT ANALYSIS BY GAS CHROMATOGRAPHY | |
|---|---|
| Ethanol | 6.7 area % |
| Chloropropylmethoxydiethoxysilane | 1.02 area % |
| Chloropropyltriiethoxysilane | 90.7 area % |

Chloropropyltriethoxysilane Reaction with Na₂S₄

The chloropropyltriethoxysilane made from transesterification of the corresponding methyl ester was used as the raw material to make 3,3'-bis (trialkoxysilylpropyl) tetrasulfide. A charge of 145.97 grams of the chloropropyltriethoxysilane prepared above was added to the addition funnel. Chloropropyltriethoxysilane addition was begun when the reactor started to reflux. This reaction was conducted over a period of 46 minutes.

Recovery of Product

At the end of the reaction, the material in the reactor was red with orange suspended solids. The system was held at reflux for 1.5 hours. The reactor was cooled to 25° C. and held overnight for filtration. The reactor contents were filtered through a pressure filter equipped with 0.25 μ filter pad. The filter cake was washed with 635 grams of acetone and dried overnight. The product was then ethanol stripped by charging 318.54 of filtrate to the reactor, and applying a vacuum to 100 mm Hg.

Finally, the reactor contents from the strip step were filtered through a 0.25 μ filter pad to yield 143.39 grams of product. The product was analyzed by gas chromatography (GC), for % sulfur, solvent pH, sodium concentration, and color (GVS), with the following results:

| GC Analysis of Product Sample | |
|---|---|
| Component | Area % |
| EtOH | 0.46 |
| Chloropropyltriethoxysilane | 0.45 |
| 3-mercaptopropyltriethoxysilane | 1.3 |
| 3-Sulfur Product | 26 |
| 4-Sulfur Product | 68.6 |
| % S | 22.4 |
| Solvent pH | 6.3 |
| Sodium | 0.26 ppm |
| Color (GVS) | 10–11 |

The above description is for the purpose of teaching the person of ordinary skill in the art how to practice the present invention and it is not intended to detail all of those obvious modifications and variations of it which will become apparent to the skilled worker upon reading the description. It is intended, however, that all such obvious modifications and variations be included within the scope of the present invention which is defined by the following claims. The claims cover the indicated components and steps in all arrangements and sequences which are effective to meet the objectives intended for the invention, unless the context specifically indicates the contrary.

I claim:

1. A process for the preparation of silane polysulfides, the process comprising:

(a) contacting hydrogen sulfide gas with an active metal alkoxide solution, (b) reacting elemental sulfur with the product of step (a), and (c) reacting the product of step (b) with a halohydrocarbylalkoxysilane of the formula Q—R—X in which Q is

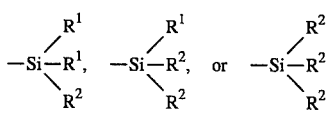

and in which

R¹ is an alkyl group of 1 to 4 carbon atoms or phenyl, and

R² is an alkoxy group with 1 to 8, preferably 1 to 4, carbon atoms, a cycloalkoxy group including 5 to 8 carbon atoms, or a straight or branched chain alkylmercapto group with 1 to 8 carbon atoms, wherein the various R¹ and R² groups can be the same or different, R is a divalent hydrocarbyl group including 1 to 18 carbon atoms, and X is a halogen, to produce a compound of of the formula Q—R—S$_n$—R—Q in which Q and R are as defined above, and n is an integer of from 2 to 9.

2. A process according to claim 1 wherein the product of step (c) is purified to remove salt formed during the reaction and solvent.

3. A process according to claim 1 wherein the product of step (c) is a methoxy derivative, and said methoxysilane derivative is converted to a silane derivative containing higher alkoxy groups.

4. A process according to claim 1 wherein Q is

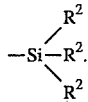

5. A process according to claim 1 wherein $R^2$ is ethoxy.

6. A process according to claim 1 wherein n is within the range of from 3 to 5.

7. A process according to claim 1 wherein the active metal alkoxide is sodium ethoxylate.

8. A process according to claim 1 wherein the halogen is chlorine.

9. A process according to claim 1 wherein R is 1,3-propylene.

10. A process for the preparation of $(C_2H_5O)_3Si(CH_2)_3—S_4—(CH_2)_3Si(OC_2H_5)_3$, the process comprising:

(a) contacting an ethanol solution of sodium ethoxylate with hydrogen sulfide gas to produce a solution of $Na_2S$, (b) adding elemental sulfur to the solution of $Na_2S$ in an amount sufficient to form $Na_2S_4$, and (c) adding $Cl(CH_2)_3Si(C_2H_5O)_3$ to the resulting reaction mixture and reacting to completion.

* * * * *